US006252123B1

(12) United States Patent
Miller et al.

(10) Patent No.: US 6,252,123 B1
(45) Date of Patent: Jun. 26, 2001

(54) MEMBRANE SEPARATION PROCESS FOR METAL COMPLEX CATALYSTS

(75) Inventors: Jay Fingeret Miller; Joan Ayer Rodberg, both of Charleston; Brian Michael Roesch, Cross Lanes; George Ernest Keller, II, South Charleston; Lisa Evans Curry, Hurricane, all of WV (US); Paul Frank Bryan, Mt. Vernon, IN (US); John Edward Davis, Charleston; James Charles Hatfield, St. Albans, both of WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/350,073

(22) Filed: Jul. 8, 1999

Related U.S. Application Data

(60) Provisional application No. 60/092,216, filed on Jul. 9, 1998.

(51) Int. Cl.[7] ................... C07C 47/058; C07C 47/09; C07C 45/50
(52) U.S. Cl. ................... 568/492; 568/451; 568/454; 210/500.25
(58) Field of Search ................... 568/454, 451, 568/492; 210/500.25

(56) References Cited

U.S. PATENT DOCUMENTS

| | | | |
|---|---|---|---|
| 4,189,380 | 2/1980 | Booth et al. | 210/23 |
| 4,200,714 | 4/1980 | Mahoney et al. | 526/28 |
| 4,560,746 | 12/1985 | Rebhahn et al. | 534/840 |
| 4,857,078 | 8/1989 | Watler | 55/16 |
| 5,139,541 | 8/1992 | Edlund | 55/16 |
| 5,199,962 | 4/1993 | Wijmans | 55/16 |
| 5,215,667 | * 6/1993 | Livingston et al. | 210/651 |
| 5,259,870 | 11/1993 | Edlund | 95/56 |
| 5,554,286 | 9/1996 | Okamoto et al. | 210/500 |
| 5,670,051 | 9/1997 | Pinnau et al. | 210/651 |

OTHER PUBLICATIONS

Catalysis with Permselective Iorganic Membranes, 1989 Elsevier Science Publishers B.V. J.N. Armor (pp. 1–25).
Inorganic Membranes: The New Industrial Revolution Douglas E. Fain, Oak Ridge K–25 Site Martin Marietta Energy Systems, Inc., (1995).

\* cited by examiner

*Primary Examiner*—Sreeni Padmanabhan
(74) *Attorney, Agent, or Firm*—G. T. Hampilos

(57) ABSTRACT

This invention relates to a process for the separation of a metal complex catalyst and any free ligand which may be present, from a homogeneous organic synthesis reaction mixture using sub-nanoporous, chemically stable membranes having discrete pores which allow organic products and by-products to pass through the membrane as permeate while retaining substantially all of the metal complex catalyst and free ligand, if any, as retentate.

3 Claims, No Drawings

MEMBRANE SEPARATION PROCESS FOR METAL COMPLEX CATALYSTS

This application claims benefit of Provisional Application No. 60/092,216 filed Jul. 9, 1998.

This invention relates to the separation and retention of metal complex catalysts from homogeneous organic and/or aqueous reaction mixtures present in known organic synthesis processes using sub-nanoporous, chemically stable membranes. The membrane separation process of this invention is particularly useful to separate an organic solubilized rhodium-organophosphite or organophosphine carbonyl complex catalysts and free organophosphite or organophosphine ligands from a homogeneous non-aqueous hydroformylation reaction mixture which may contain, in addition to said catalyst and free ligand, aldehyde product, alcohols, unreacted olefin feed, synthesis gas, high boiling by-products, and an organic solvent.

BACKGROUND OF THE INVENTION

A number of known organic synthesis processes require separation and recovery of expensive complex metal catalysts from a homogeneous organic and/or aqueous reaction mixture. Such processes include hydroformylation, hydrocylation (intramolecular and intermolecular), hydrocyanation, hydroamidation, hydroesterification, aminolysis, alcoholysis, carbonylation, olefin isomerization, transfer hydrogenation and the like. Many of these processes involve reaction of organic compounds with carbon monoxide, or with carbon monoxide and additional reactants such as hydrogen, or with hydrogen cyanide, in the presence of a suitable metal complex catalyst. Such processes, including the identification of suitable reactants and process conditions are well known in the chemical art and are described in various literature references such as Kirk-Othmer, Encyclopedia of Chemical Technology, Fourth Edition, 1996.

The metal complex catalysts useful in such organic synthesis processes are also well known and described in the literature. Such catalysts generally comprise an appropriately selected metal which is complexed with one or more suitable ligands. Examples of metals which can be used in such processes include Group 8, 9 and 10 metals such as rhodium (Rh), cobalt (Co), iridium (Ir), ruthenium (Ru), iron (Fe), nickel (Ni), palladium (Pd), platinum (Pt), osmium (Os) and mixtures thereof. Other useful metals include Group 6 metals such as chromium (Cr), molybdenum (Mo), tungsten (W) and mixtures thereof. The preferred and most commonly used metals are rhodium, cobalt and ruthenium, especially rhodium. A wide variety of compounds useful as ligands in the metal complex catalysts are also well known in the art and described in the literature. Phosphorus containing organic compounds have been found to be particularly useful as ligands.

While the membrane separation process of this invention can be usefully applied to the separation and recovery of metal complex catalysts in any of the organic synthesis processes identified above, it will be described and illustrated in detail as used in hydroformylation processes.

Methods for producing aldehyde products by hydroformylation of an olefin with carbon monoxide and hydrogen (more commonly referred to as synthesis gas or syn gas) in the presence of a metal complex catalyst are well known in the art as exemplified by U.S. Pat. No. 3,420,898 (cobalt complexes), U.S. Pat. No. 4,148,830 (rhodium-organophosphine complexes) and U.S. Pat. Nos. 4,599,206; 4,668,651; and 4,769,498 (rhodium-organophosphite complexes). In such processes the desired aldehyde product is separated and recovered from the reaction medium by suitable known techniques such as distillation or fractionation and a residue containing catalyst-ligand complex and possibly free ligand is recovered and returned to the reactor. Effective separation and recovery of the desired aldehyde product from its hydroformylation reaction medium with minimal loss of the expensive metal catalyst or ligand is extremely important to the commercial success of any hydroformylation process.

The harsh conditions often associated with conventional techniques such as distillation for separating a desired organic synthesis product, such as the aldehyde product in a hydroformylation process, from its reaction medium containing the metal complex catalyst can have a deleterious effect on catalyst activity resulting in unacceptable catalyst or ligand losses. This problem is particularly severe in certain organic synthesis processes such as the hydroformylation of longer chain olefinic compounds for producing the corresponding higher molecular weight aldehydes. Increased temperatures and harsher conditions are necessary to volatilize higher molecular weight aldehyde products during separation from the hydroformylation reaction product medium which may eventually lead to excessive loss (via chemical and thermal degradation) of catalyst or ligand, particularly over the normally prolonged periods of continuous reaction time required for a successful commercial operation.

A similar problem is presented when higher boiling by-products are formed in the organic synthesis reaction. For example, aldehyde condensation by-products such as trimers and tetramers, may be formed during a hydroformylation reaction and would need to be separated from catalyst-containing hydroformylation recycle residues after separate recovery of the hydroformylation aldehyde product.

Thus, the discovery of a simpler, more gentle, procedure that would allow for separation of organic product and by-products from organic synthesis reaction mixtures, particularly those containing higher molecular weight organic products and high boiling by-products, while retaining essentially all of the metal complex catalyst and any free ligand which may be present while avoiding potential catalyst and ligand degradation problems attendant with conventional separation techniques such as distillation, would obviously be highly beneficial to the art. It is believed that such a discovery is provided by the process of the present invention which relates to the novel use of particular sub-nanoporous, chemically stable membranes to retain essentially all metal complex catalyst and any free ligand while separating a desired organic product from its reaction medium.

The use of the various polymeric membrane systems to retain homogeneous metal complex catalysts while separating aldehyde product from hydroformylation reaction mediums has been proposed in the prior art literature. Such separation processes typically comprise bringing a liquid hydroformylation reaction medium which contains a homogeneous metal complex catalyst and possibly free ligand dissolved therein into intimate contact with a semipermeable polymeric membrane, which allows a portion of aldehyde product and unreacted olefin feed to pass through the membrane, while retaining a substantial portion of the metal complex catalyst.

By way of example, U.S. Pat. Nos. 5,215,667; 5,288,818; 5,298,669; are all directed to the use of a hydrophobic polymeric membrane to separate water-soluble Group VIII noble metal ionic phosphine ligand complex catalysts from aldehyde containing hydroformylation reaction mediums comprising aqueous solutions, emulsions or suspensions of said catalysts. U.S. Pat. No. 5,395,979 is directed to separating a homogeneous hydrocarbon soluble rhodium-alkylated or arylated phosphine complex catalyst from a crude aldehyde containing hydroformylation reaction product using a dense, polymeric, nonpolar membrane. A series of British patents propose separating transition metal complexes, e.g. rhodium-trialkylphosphine complex hydroformylation catalysts, from a reaction solution by bringing the solution into contact with one side of a polymeric membrane, e.g. a cellulosic membrane (B.P. 1,243,507 which corresponds to U.S. Pat. No. 3,617,553), a silicone rubber membrane (B.P. 1,243,508), a polyolefin membrane (B.P. 1,260,733) or a polyamide membrane (B.P. 1,266,180). Likewise, British Patent 1,312,076 proposes to use the same membranes to separate hydroformylation transition metal catalysts from a liquid side stream of the high boiling by-products of the hydroformylation process after removal of the aldehyde product via distillation.

British Patent 1,432,561 proposes a process for the hydroformylation of olefins which comprises reacting an olefin at elevated temperature and pressure with carbon monoxide and hydrogen in the presence of a catalyst complex of a Group VIII metal (e.g. cobalt or rhodium) and a biphyllic ligand of trivalent phosphorus, arsenic or antimony to give a crude liquid hydroformylation product containing an aldehyde and/or alcohol, separating aldehyde and/or alcohol from the crude product and leaving a liquid, and bringing the liquid optionally after separation of the Group VIII metal compound and substantially free from aldehyde and alcohol, under reverse osmosis conditions into contact with one side of a silicone rubber semi-permeable membrane in which the polymer chains have been at least partly cross-linked by gamma-radiation, whereby the liquid retained by the membrane contains a higher concentration of the Group VIII metal compound and/or biphyllic ligand than the original liquid.

Dutch Patent No. 8700881 proposes an improved membrane process for separating Group VIII metal hydroformylation catalysts (e.g. cobalt or rhodium-organophosphine complexes) and free phosphine ligand from their crude aldehyde product containing hydroformylation mixtures which comprises employing membranes of silicone rubber or modified derivatives there of in combination with an aromatic deswelling agent such as nonpolar hydrocarbons which contain no oxygen or halogen, U.S. Pat. No. 5,174,899 suggests that semi-permeable polymeric membranes of aromatic polyamides can be used to separate metal complex catalysts from organic solvents, e.g. rhodium-triphenylphosphine or phosphane and ammonium salts of sulfonated or carboxylated triarylphosphanes from hydroformylation aldehyde product mixtures.

European Patent No 0263953, published on Aug. 29, 1986 discloses a process for separating a water-soluble, noble metal catalyst complex from an aqueous solution using a polymeric membrane such as a cellulose acetate membrane. According to this process, volatile organic substances such as aldehyde product, are removed from the reaction medium by, for example, distillation, before the remaining aqueous solution is subjected to a membrane separation treatment.

While the polymeric membranes disclosed in the prior art discussed above are capable of retaining metal complex catalysts while separating aldehyde product from a hydroformylation reaction medium, they have serious deficiencies which detract from their suitability for use in many commercial hydroformylation processes. In particular, such polymeric membranes rely heavily on a solution-diffusion transport mechanism to selectively pass aldehyde product, unreacted olefin feed and high boiling by products through the membrane while retaining the noble metal complex catalyst. The rate of permeation for such membranes is often insufficient to provide economical separation and retention of catalyst in commercial processes. In addition, these prior art polymer membranes often do not possess adequate chemical and structural stability when exposed to severe hydroformylation reaction mixtures and process conditions to avoid having to be replaced more frequently than is desirable in a commercial operation.

Another approach to separating noble metal complex hydroformylation catalysts from high boiling products and by products involves an attempt to create very high molecular weight catalyst complexes which can be separated by ultrafiltration, i.e. by using membranes having pore diameters of 50 A° or greater. See Imayanitov et al, All-Union Scientific Research Institute of Petrochemical Processes, Neftekhimiya, 32, No. 3:200–7 (May–June 1992). Noble metal complex catalyst prepared in this manner do not perform satisfactorily in commercial hydroformylation operations. The membrane separation process of the present invention is capable of separating normal noble metal complex catalyst molecules from other organic molecules in a homogeneous hydroformylation reaction mixture without the necessity of attaching the complex catalyst molecules to a polymer backbone.

SUMMARY OF THE INVENTION

This invention can broadly be described as a process for separating organic synthesis products and by-products from a homogeneous reaction mixture, for example, a hydroformylation reaction mixture which contains aldehyde product and which may additionally contain unreacted olefin feed, alcohols, high boiling by-products, synthesis gas and solvent while retaining solubilized metal complex catalyst and any free ligand which may be present, by bringing said reaction mixture into contact with a sub-nanoporous, chemically stable membrane. The sub-nanoporous membranes used in the process of the present invention are characterized by being composed of discrete pores providing pathways through the membrane, substantially all of said pathways having a limiting pore diameter of less than the diameter of the smallest molecule of noble metal complex catalyst or free ligand, said membranes being further characterized by having a narrow limiting pore diameter distribution of less than ±30% of the average limiting pore diameter. In certain applications, depending on the size of the molecules to be separated, the membranes may be composed of discrete pores providing pathways substantially all of which have limiting pore diameters of less than 30 A°, preferably less than 15 A° and limiting pore diameter distributions as narrow as ±10% of the average limiting pore diameter. The sub-nanoporous membranes used in the separation process of this invention can be made from any suitable chemically stable material such as ceramics, metals and inorganic polymeric materials which are resistant to degradation in the presence of organic chemicals under hydroformylation or other organic synthesis process conditions.

DETAILED DESCRIPTION INCLUDING THE PREFERRED EMBODIMENTS

The separation process of the present invention will be described in detail as used in hydroformylation reactions but its applicability to other organic synthesis reactions employing metal complex catalysts will be readily apparent to one skilled in the art.

Hydroformylation reactions involve the conversion of olefins to desired aldehyde products containing at least one additional carbon atom by reacting the olefin with carbon monoxide and hydrogen in the presence of a metal complex catalyst. The reaction medium in commercial versions of hydroformylation processes is typically a homogeneous mixture of olefin feed, carbon monoxide, hydrogen, solvent, aldehyde product, by-products, a metal complex catalyst and in some instances free excess ligand. Separation and recovery of the aldehyde product without loss or degradation of the metal complex catalyst and free ligand is an important element of an economically acceptable process. Any of the metal complex catalysts described in patents or other literature as useful in hydroformylation reactions whose molecular size is larger than the molecular size of the aldehyde product and other organic constituents which make up the hydroformylation reaction mixture are capable of being separated from the aldehyde product by the membranes of the present invention. In commercial hydroformylation processes, such catalysts are typically ligand containing cobalt or rhodium complexes with the amount of metal present in the reaction mixture typically ranging from 25 to 2000 ppm by weight. The details of any particular hydroformylation process such as the type of reactants, reaction conditions, and catalyst chemistry other than the molecular size of the noble-metal catalyst complex and any free ligand to be recovered, are not critical features of the present invention. However, an important feature of the membranes used in the separation process of the present invention are their ability to withstand the harsh conditions, including high temperatures and pressures, encountered in many hydroformylation processes.

By way of example, a particular hydroformylation process in which the membrane separation technique of the present invention may be usefully employed involves the production of aldehydes by reacting an olefinic compound with carbon monoxide and hydrogen in the presence of a solubilized rhodium-organophosphite complex catalyst and excess free organophosphite ligand in a liquid medium that also contains a solvent for the catalyst and ligand. Such a hydroformylation process and the organophosphite ligands used are described in detail in U.S. Pat. No. 5,681,473, the entire contents of which are incorporated herein by reference.

In the hydroformylation processes described in the prior art, and particularly those that are practiced commercially, the molecular size of metal complex catalyst and free ligand itself has been found to be greater than the molecular size of the aldehyde product and other organic constituents of the reaction mixture. While the molecular size of the complex catalyst and the free ligand itself could be larger, it is usually found to be less than 30 A° in diameter and may be as small as 10 A° or less.

The separation process of the present invention involves the steps of (a) contacting the homogeneous reaction mixture from a metal complex catalyzed hydroformylation reaction with a sub-nanoporous, chemically stable membrane which is composed of discrete pores providing pathways through the membrane, substantially all of said pathways having a limiting pore diameter of less than the diameter of the smallest molecule of complex catalyst or free ligand, if any, said membrane having a narrow limiting pore diameter distribution of less than ±30% of the average limiting pore diameter of said pathways, (b) recovering organic products and by-products as permeate, and (c) retaining at least ninety-nine percent (99%) by weight of the metal complex catalyst and free ligand, if any as retentate. In a preferred embodiment, substantially all of the pores providing discrete pathways through the membrane have a limiting pore diameter of 15 A° or less and a limiting pore diameter distribution no greater than ±10% of the average limiting pore diameter. If necessary to accomplish the desired molecular separation, membranes composed of discrete pores providing pathways through the membrane having limiting pore diameters as small as 4 A° or less can be used in the separation process of the present invention.

The separation process can be performed batchwise or continuously, in one or more stages. In commercial processes, continuous operation is preferred. Although the membrane separation process could be performed within the hydroformylation reactor, it is normally performed outside of the reactor so that reaction conditions and separating conditions, e.g. temperature and pressure, can be optimized independently of each other. The hydroformylation reaction mixture could be subjected to treatments such as distillation to remove aldehyde product or by-products before conducting the membrane separation. For example, it may be advantageous to perform a distillation to remove a portion of unreacted monomer and aldehyde product from the reaction mixture before using the membrane separation process of this invention to recover metal complex catalyst from the remaining reaction mixture. However, to avoid catalyst degradation and to maintain the catalyst in its active form for reuse, the membrane separation process may be performed first. The retentate containing concentrated catalyst solution may be returned to the hydroformylation reactor while the permeate may be subjected to further treatment to purify the aldehyde product.

The separation process of the present invention is preferably a pressure-driven process. Typically, the pressure of the hydroformylation reaction mixture subjected to the membrane separation process will range from a low of about 50 pounds per square inch and to a high of about 1500 pounds per square inch. More preferably the pressure of the hydroformylation reaction mixture subjected to the membrane separation process is from about 100 psi to about 600 psi. The permeate which has passed through the membrane, is at a greatly reduced pressure.

The membranes used in the separation process of the present invention may be made of any suitable material which is chemically and structurally stable in the harsh environment and under the rigorous operating conditions of many organic synthesis reactions such as, for example, a commercial hydroformylation process. Preferably, the membranes will be constructed of a suitable inorganic material such as metals, metal alloys, metal oxides or aluminosilicates such as zeolites. Suitable metals and their alloys include iron, nickel, copper, chromium, titanium, molybdenum tungsten, aluminum, gold, silver and platinum. Metal oxides which may be used in the preparation of membranes for the separation process of the present invention include silica, alumina, zirconia and titania Useful zeolites may be selected from various mineral or synthetic types which are suitably stable upon dehydration and possess acceptable porosity characteristics. By way of example and without limitation, zeolite types exhibiting suitable stability when dehydrated, include eronite, offretite, sodalite hydrate, mordenite, A, NA, X, Y, L, F, ZK-4 and ZK-5.

Membranes useful in the separation process of the present invention may be supported or unsupported. However, thinner sub-nanoporous membrane layers may be used in the separation process of the present invention when such layer is applied to a microporous support, or the membrane layer is formed as a thin-skin on a microporous support layer of the same material to provide the supported structure. Such supported sub-nanoporous membrane structures or integrally thin-skinned structures normally provide higher permeation rates and better mechanical stability than unsupported membranes and thus are preferred for most applications. Suitable supported sub-nanoporous membrane structures are prepared by forming a thin layer of the selected metal, metal oxide or zeolite having the desired pore configuration on a microporous support using known techniques. Useful porous supports can be made from a variety of materials such as metals (e.g. stainless steel, titanium, aluminum, silver etc.), ceramics (e.g. alumina, silica, zirconia, etc.) and chemically resistant polymers such as polytetraflouroethylene . Preferably, the support will be made of a microporous ceramic or sintered metal which is the same as or otherwise very compatible with the material in the membrane layer. The porous support should preferably have a porosity of 0.1% to 80% and an average pore diameter of 0.01 µm to 100 µm to provide acceptable separating factors and permeation rates and mechanical stability.

A number of known techniques may be used to apply a thin sub-nanoporous membrane layer having the desired pore configuration to the surface of a suitable support structure. One technique involves applying a thin layer of powdered metal mixed with a suitable polymer on the surface of a microporous support structure and subjecting the coated support to a high temperature sintering operation to burn off the polymer leaving the support surface coated with a thin sub-nanoporous layer of the selected metal. By controlling the size and size distribution of the particles in the metal powder and the amount of polymer in the mixture, a sub-nanoporous layer of the selected metal containing the desired pore configuration will be obtained after the sintering operation.

Another known technique which may be used to create the sub-nanoporous membrane layer to be used in the separation process of the present invention involves sputtering the surface of a suitable support structure with an atomized spray of extremely fine metal particles while applying a very high voltage charge to the support structure. The atomized spray of metal particles may be generated by flowing molten metal through a very small orifice using extremely high pressures such as those resulting from exploding a gun behind the molten metal. This technique could also be used to create a sub-nanoporous ceramic membrane by spraying a solution of the ceramic through a very small orifice using the same type of exploding gun.

Another technique described in the literature which may be used to create a sub-nanoporous membrane useful in the separation process of the present invention involves sputtering a thin layer of suitable metal, e.g. gold, onto a support structure and then placing the structure into a scanning, tunneling microscope where the gold atoms are moved leaving open pores of the desired configuration.

Membrane composites useful in the separation process of the present invention which contain sub-nanoporous layers of a zeolite material may be prepared by the process described in U.S. Pat. No. 5,554,286. Membrane composites containing a sub-nanoporous layer of zeolite material which may be useful are commercially available from the Smart Chemical Company, Ltd., London, England.

Although the invention has been illustrated by the preceding detailed description, it is not to be construed as being limited thereby. Modifications and variations of this invention will be obvious to a worker skilled in the art and it is to be understood that such modifications and variations are to be included within the purview of this application and the spirit and scope of the appended claims.

What is claimed is:

1. A process for separating solubilized metal complex catalyst and any free ligand which may be present, from a homogeneous organic synthesis reaction mixture containing hydroformylation products and by-products, which comprises:

(a) contacting said homogeneous hydroformylation synthesis reaction mixture with a sub-nanoporous chemically stable membrane which is composed of discrete pores providing pathways through the membrane, substantially all of said pathways having a limiting pore diameter which is less than the diameter of the smallest molecule of metal complex catalyst or free ligand, if any, present in said reaction mixture, said membrane having a narrow limiting pore diameter distribution of less than ±30% of the average limiting pore diameter of said pathways;

(b) recovering said organic products and by-products as a permeate; and (c) retaining at least ninety-nine percent (99%) of the metal catalyst complex and free ligand, if any, as retentate.

2. The process of claim 1 wherein said limiting pore diameter is less than 30 A°.

3. The process of claim 1 wherein said limiting pore diameter is less than 15 A°.

* * * * *